(12) United States Patent
Chung

(10) Patent No.: US 12,251,238 B2
(45) Date of Patent: Mar. 18, 2025

(54) COMBINATION TABLE AND CUP WITH BIO-SIGNAL ACQUISITION AND FEEDBACK CAPABILITIES

(71) Applicant: HAOSEN TECH CO., LTD., New Taipei (TW)

(72) Inventor: Kuo-Yuan Chung, New Taipei (TW)

(73) Assignee: HAOSEN TECH CO., LTD., New Taipei (TW)

( * ) Notice: Subject to any disclaimer, the term of this patent is extended or adjusted under 35 U.S.C. 154(b) by 558 days.

(21) Appl. No.: 17/584,321

(22) Filed: Jan. 25, 2022

(65) Prior Publication Data
US 2022/0142580 A1 May 12, 2022

Related U.S. Application Data

(63) Continuation-in-part of application No. 16/565,508, filed on Sep. 10, 2019, now abandoned.

(51) Int. Cl.
| | |
|---|---|
| A61B 5/00 | (2006.01) |
| A61B 5/0205 | (2006.01) |
| A61B 5/021 | (2006.01) |
| A61B 5/024 | (2006.01) |
| A61B 5/1455 | (2006.01) |
| A61B 5/16 | (2006.01) |
| A61B 5/339 | (2021.01) |

(52) U.S. Cl.
CPC .......... *A61B 5/6887* (2013.01); *A61B 5/0006* (2013.01); *A61B 5/0008* (2013.01); *A61B 5/002* (2013.01); *A61B 5/02055* (2013.01); *A61B 5/021* (2013.01); *A61B 5/02405* (2013.01); *A61B 5/02427* (2013.01); *A61B 5/14552* (2013.01); *A61B 5/165* (2013.01); *A61B 5/339* (2021.01); *A61B 5/7275* (2013.01); *A61B 5/746* (2013.01); *A61B 2560/0219* (2013.01); *A61B 2562/0271* (2013.01)

(58) Field of Classification Search
None
See application file for complete search history.

*Primary Examiner* — Lynsey C Eiseman
*Assistant Examiner* — Jessica L Mullins
(74) *Attorney, Agent, or Firm* — Li & Cai Intellectual Property Office

(57) ABSTRACT

A combination table and cup with bio-signal acquisition and feedback capabilities includes a table and a cup placed on the table. The cup includes a first electrode, a second electrode, a human-body temperature sensor module, a PPG sensor module, a bio-signal acquisition module, an NFC transmitter and a wireless charging receiver. The table includes a table top having a transparent cover plate, one or more transceiver modules each having an NFC receiver and a wireless charging transmitter, a visual display device and a computing device. The transparent cover plate is embedded in the table top. One or more contact areas are formed on a top surface of the table top. The transceiver module of the table is arranged corresponding to the position of the contact area and is configured to transmit electrical power and receive bio-signals when the cup is placed on the contact area.

10 Claims, 11 Drawing Sheets

COMBINATION TABLE AND CUP WITH BIO-SIGNAL ACQUISITION AND FEEDBACK CAPABILITIES

CROSS-REFERENCE TO RELATED PATENT APPLICATION

This Application is a Continuation-in-Part of application Ser. No. 16/565,508 filed Sep. 10, 2019, now pending, and entitled bio-feedback cup with bio-signal acquisition and feedback capabilities.

FIELD OF THE DISCLOSURE

The present disclosure relates to a combination table and cup, and more particularly to a combination table and cup with bio-signal acquisition and feedback capabilities.

BACKGROUND OF THE DISCLOSURE

In recent years, since the importance of health has been emphasized, people wear various smart wearable devices, such as wristwatches or wristbands, to measure their daily bio-signals, and those devices serve as an important interface for tracking of bio-signals and cardio-health management. However, for people who don't wear wristwatches in their daily lives, wearing such devices becomes a burden, forcing them to adapt to unfamiliar materials or giving up their favorite clothing coordination. Therefore, if the measurement interface of the bio-signals can be an item people use every day, it will not cause any additional burden on people, or force them to change their habits or clothing coordination. Measurement behavior is always considered repetitive, boring, and not directly beneficial, so that people often lose the motivation to continuously conduct measurements and long-term tracking. Therefore, incorporating such tedious measurements into people's daily lives has always been an issue to be solved. The present disclosure provides a combination that can easily achieve daily psychological and physical health management.

SUMMARY OF THE DISCLOSURE

One of the objectives of the present disclosure is to provide a combination table and cup with bio-signal acquisition and feedback capabilities that can overcome the aforementioned drawbacks.

In one aspect, the present disclosure provides a combination table and cup with bio-signal acquisition and feedback capabilities, including a cup and a table. The cup includes a first electrode, a second electrode, a human-body temperature sensor module, a photoplethysmography (PPG) sensor module, a bio-signal acquisition module, a near field communication (NFC) transmitter and a wireless charging receiver. The first electrode, the second electrode, the human-body temperature sensor module and the PPG sensor module are exposed on a surface of the cup, and the bio-signal acquisition module, the NFC transmitter and the wireless charging receiver are concealed within an internal waterproof space of the cup. The bio-signal acquisition module is electrically connected to the first electrode, the second electrode, the human-body temperature sensor module, the PPG sensor module, the NFC transmitter and the wireless charging receiver. The bio-signal acquisition module is configured to detect a user's cardiac signal with a built-in electrocardiogram (ECG or EKG) acquisition module. The bio-signal acquisition module detects and obtains an ECG signal when the user touches the first electrode and the second electrode with both hands. The bio-signal acquisition module obtains a PPG signal through the PPG sensor module when the user touches the PPG sensor module. The bio-signal acquisition module obtains a human-body temperature signal through the human-body temperature sensor module when the user touches the human-body temperature sensor module. The table includes a table top having a transparent cover plate, one or more transceiver modules each having an NFC receiver and a wireless charging transmitter, a visual display device and a computing device. The table top has an upper portion, a lower portion, and an accommodation space formed between the upper portion and the lower portion. The transparent cover plate is embedded in the upper portion and made of a transparent material. One or more contact areas are formed on a top surface of the upper portion and surround the transparent cover plate. The one or more transceiver modules are arranged in the accommodation space, located at a bottom surface of the upper portion, and corresponding to the one or more contact areas in position. The visual display device is arranged in the accommodation space, located on a top surface of the lower portion and underneath the transparent cover plate. The computing device is arranged in the accommodation space and located on the top surface of the lower portion. The computing device is electrically connected to the one or more transceiver modules and the visual display device. The wireless charging transmitter is configured to transmit electrical power through an inductive coupling to the wireless charging receiver when the cup is placed on the corresponding contact area. The NFC receiver is configured to receive the ECG signal, the PPG signal and the human-body temperature signal transferred from the NFC transmitter through a near field communication protocol when the cup is placed on the corresponding contact area. The computing device is configured to provide a physiological index and an extended cardiac index of the user according to the ECG signal, the PPG signal and the human-body temperature signal, and control the visual display device to display a first visual information corresponding to the physiological index and the extended cardiac index, and then determine whether to control the visual display device to display a different second visual information after comparing a value of the physiological index or the extended cardiac index with a threshold value.

Preferably, the table can further include a plurality of actuators and a plurality of indicators. The actuators and the indicators are arranged in the accommodation space and underneath the transparent cover plate. The indicators are respectively disposed on the actuators, and the computing device is electrically connected to the actuators and configured to control the actuators to drive the indicators to move in different motion trajectories.

Preferably, the actuator is an electric motor-operated actuator.

Preferably, the transparent material is a glass or a high-transparency plastic material.

Preferably, the contact area is formed by a self-luminous material.

Preferably, the physiological index that can be used as instant feedback to the user and can be recorded, includes any one or more of human-body temperature, heart rate (beats per minute, BPM), heart rate variability (HRV), peripheral oxygen saturation (SpO2), heart age, blood pressure estimates and risk alert for excessive heart rate.

Preferably, the extended cardiac index that can be determined by a preset algorithm according to physiological data, ECG data and PPG data of the user, is a mood index, a stress index, a caffeine intake index or a heart risk index.

Preferably, the computing device of the table is provided with a built-in power module. The power module is a replaceable battery module or a rechargeable battery module.

Preferably, the computing device of the table is electrically connected to an external power source.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
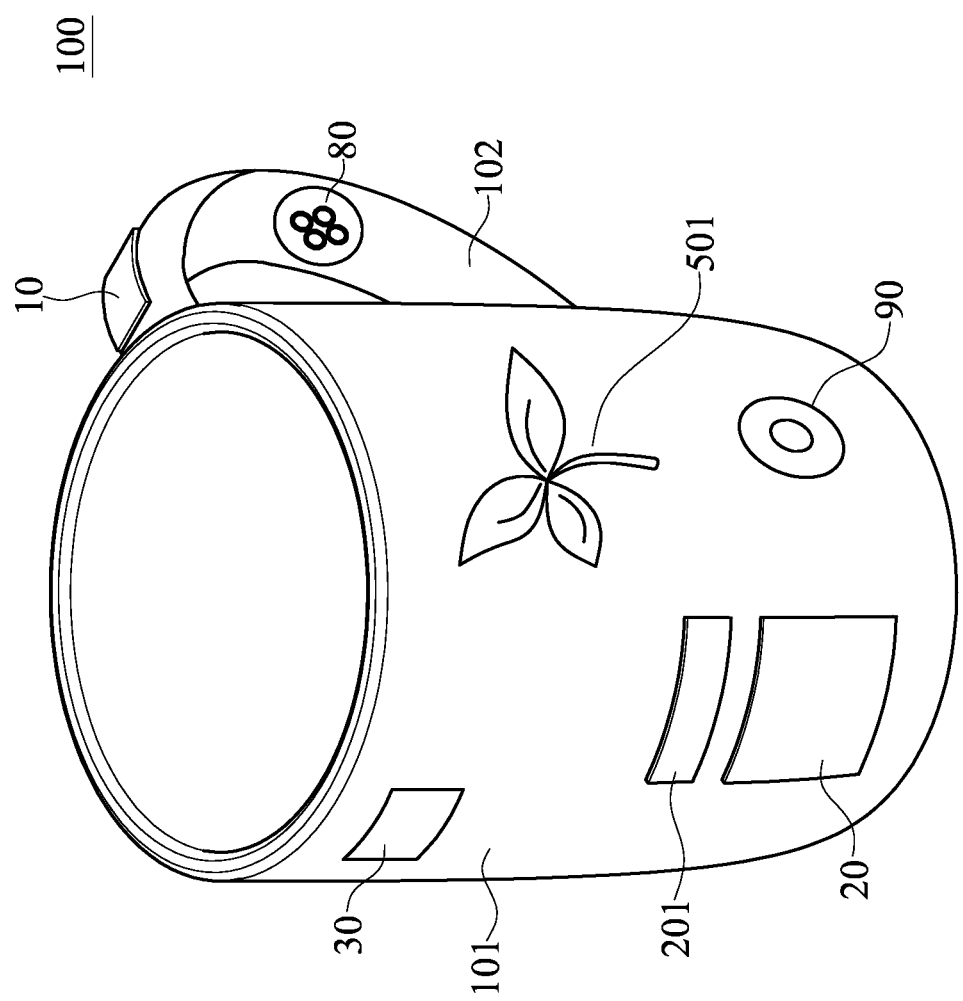
FIG. 1 is a perspective view of a cup of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Referring to FIG. 1 to FIG. 4, the present disclosure provides a bio-feedback cup with bio-signal acquisition and feedback capabilities 100.

The bio-feedback cup with bio-signal acquisition and feedback capabilities 100 (hereinafter referred to as the cup 100) basically includes a cup body 101, a grip 102, a first electrode 10, a second electrode 20, a ground electrode 201, a wireless data transmission antenna 30, a bio-signal acquisition module 40, and a bio-feedback module 50. It is also possible that the cup 100 has no grip 102.

The bio-signal acquisition module 40 and the bio-feedback module 50 may be located at appropriate positions of the cup body 101 of the cup 100, or may be built-in as parts of the cup body 101. The shape of the cup body 101 can be adjusted according to practical requirements, and it can be a container without a grip, for which there is no restriction. Furthermore, in addition to the above-described modules, the cup 100 of the present embodiment may further include a wireless data transmission module 60 and a power module 70. The wireless data transmission antenna 30, the wireless data transmission module 60 and the power module 70 can be located at appropriate positions of the cup body 101 of the cup 100, or may be built-in as parts of the cup body 101. In addition, the cup 100 of the present embodiment may further include a PPG sensor module 80 and a human-body temperature sensor module 90.

The specific details of the embodiment, as well as the interaction relationships between various modules or elements, are further explained with examples below. It shall be specifically emphasized that the detailed characteristics described below are only for the convenience of those skilled in the art to more easily understand the contents of the present disclosure, and the specific implementation methods are not limited thereto.

The cup body 101 can be a liquid container integrally formed or assembled into a suitable shape that is made of a variety of materials, such as ceramics, stainless steel, and plastics. The grip 102 can be a hand-held part that is made of a variety of materials, and may be assembled on and detached from the cup body 101. The grip 102 can also be in the form of a cup sleeve or a cup holder for the cup body 101, so as to achieve the purpose of a grip for holding the cup. The first electrode 10 is located at the grip 102 connected to the cup body 101, and it can also be placed directly on the cup body 101 without the grip 102. The first electrode 10 can be a positive electrode made of a conductive material. The first electrode 10 may be made of at least one of the following: a metal sheet, a conductive silicone/film, a thin metal plating layer on the surface of the cup body 101 or the grip 102, a thin metal coating layer, a thin metal sputter coating layer, or a thin metal plating layer. Its material and shape can be adjusted according to practical requirements or the shape of the grip 102. The first electrode 10 can be electrically connected to the bio-signal acquisition module 40 through conductive paths such as metal wires, films, or coating.

The second electrode 20 is located at the side edge of the cup body 101, and can be a negative electrode made of a conductive material. The second electrode 20 may be made of at least one of the following: a metal sheet, a conductive silicone/film, a thin metal plating layer on the surface of the cup body 101 or the grip 102, a thin metal coating layer, a thin metal sputter coating layer, or a thin metal plating layer. The material and shape of the second electrode 20 can be adjusted according to practical requirements or the shape of the cup body 101. The second electrode 20 can be electrically connected to the bio-signal acquisition module 40 through conductive paths such as metal wires, films, or coating.

The ground electrode 201 is located at the grip 102 connected to cup body 101, and may also be placed on the side edge of the cup body 101, which is not limited thereto. In some embodiments, a ground electrode may be omitted. The ground electrode 201 is made of a conductive material, such as a metal sheet, a conductive silicone, a film, a coating, and the material and shape thereof may be appropriately adjusted according to practical requirements. The ground electrode 201 can be electrically connected to the bio-signal acquisition module 40 through conductive paths such as metal wires, films, or coating.

The bio-signal acquisition module 40 can be located at the bottom of the cup body 101 and electrically connected to the first electrode 10, the second electrode 20 and the ground electrode 201, respectively. The bio-signal acquisition module 40 detects and obtains the cardiac signals of the user through the first electrode 10, the second electrode 20 and the ground electrode 201. In one embodiment, the bio-signal acquisition module 40 is or has an electrocardiogram (ECG or EKG) sensing circuit or integrated circuit. When the user touches the first electrode 10 and the second electrode 20 with both hands, in cooperation with the ground electrode 201, the body (heart) and the bio-signal acquisition module 40 cooperatively form a closed-loop circuit, thereby allowing the bio-signal acquisition module 40 to detect the user's cardiac signals and instantly record the current measurement to generate an electrocardiogram. In another embodiment, the bio-signal acquisition module 40 can receive electrical signals of the PPG sensor module 80. When the user's hand touches the PPG sensor module 80, the photoplethysmography (PPG) signals of the flowing substances in the blood can be detected during the pulses of the blood vessels, thereby calculating various physiological data (physiological index) such as the heart rate or various physiological data related to the blood.

In detail, electrocardiogram (ECG or EKG) sensing is to sense cardiac signals of the user. That is, every time the heart beats and the myocardial cells are depolarized, a small electrical change can be detected on the surface of the can be captured and amplified by the ECG sensing circuit or the integrated circuit, and then the electrocardiogram can be drawn and recorded, which is well known to those skilled in the art and therefore will not be further described. Since the signals are weak and can be easily interfered with, the integrated circuits of the amplifying circuit and the filtering circuit can be integrated into the bio-signal acquisition module 40 to amplify the weak signals and reduce the noise of the signals, so as to ensure the accuracy of detection and recording.

The bio-feedback module 50 is or has a pattern 501, which can be exposed from the cup body 101, and various physiological data of the user can be displayed through the shape or color changes of the pattern 501. When the user holds the grip 102 with one hand and touches the first electrode 10, and touches the cup body 101 with the other hand while touching the second electrode 20 at the same time, the bio-signal acquisition module 40 can detect and obtain the cardiac signals of the user through ECG and PPG sensor/module to record and calculate various physiological data thereof, such as the heart rate, heart rate variability, and so on, so that the bio-feedback module 50 gives the user corresponding bio-feedback according to various physiological data. For example, the bio-feedback module 50 can instantly give the user corresponding bio-feedback by changing the color of the cup body 101, or the color, shape or the background illuminating color of the pattern 501.

Figure 5:
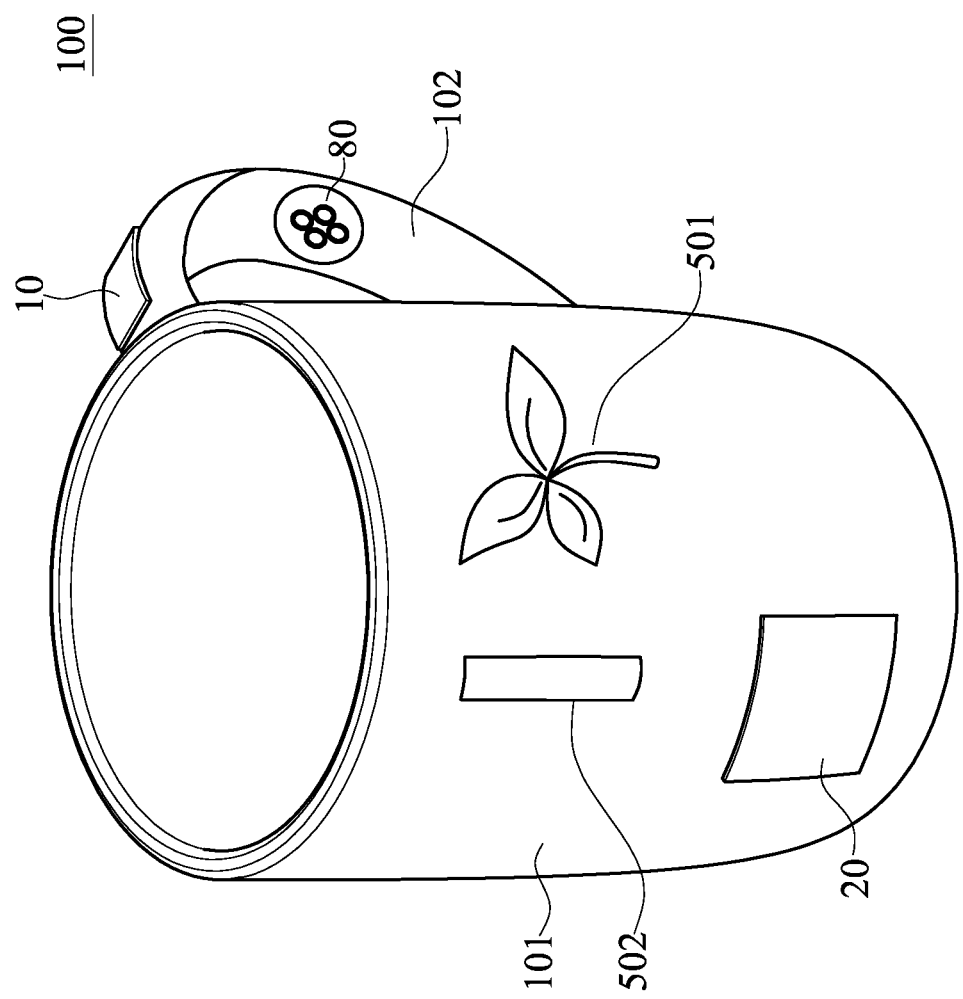
FIG. 5 is a perspective view of another cup of the present disclosure.
Figure 6:
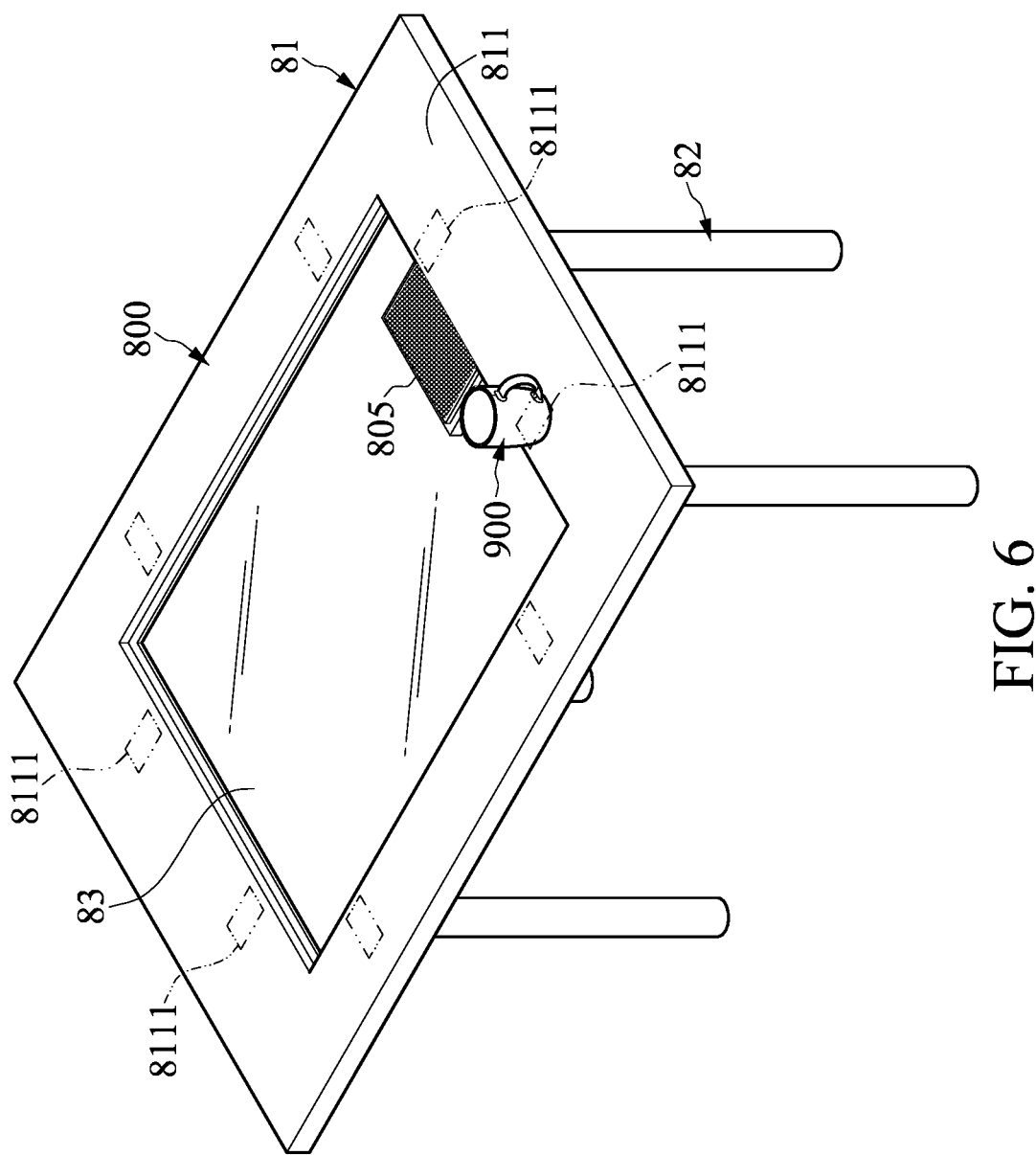
FIG. 6 is a perspective view of a combination table and cup of the present disclosure.
Figure 7:
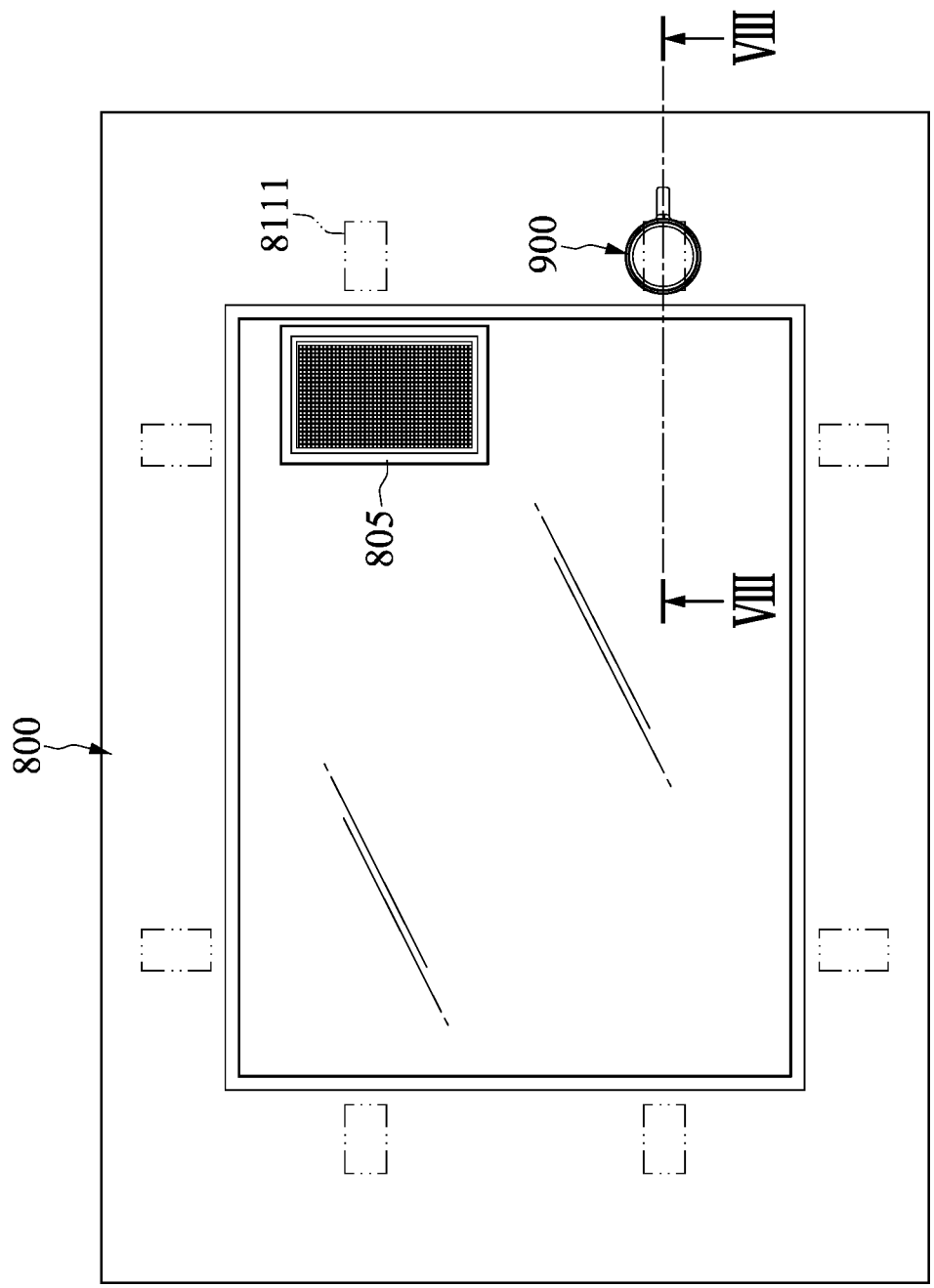
FIG. 7 is a top view of a combination table and cup of the present disclosure.
Figure 8:
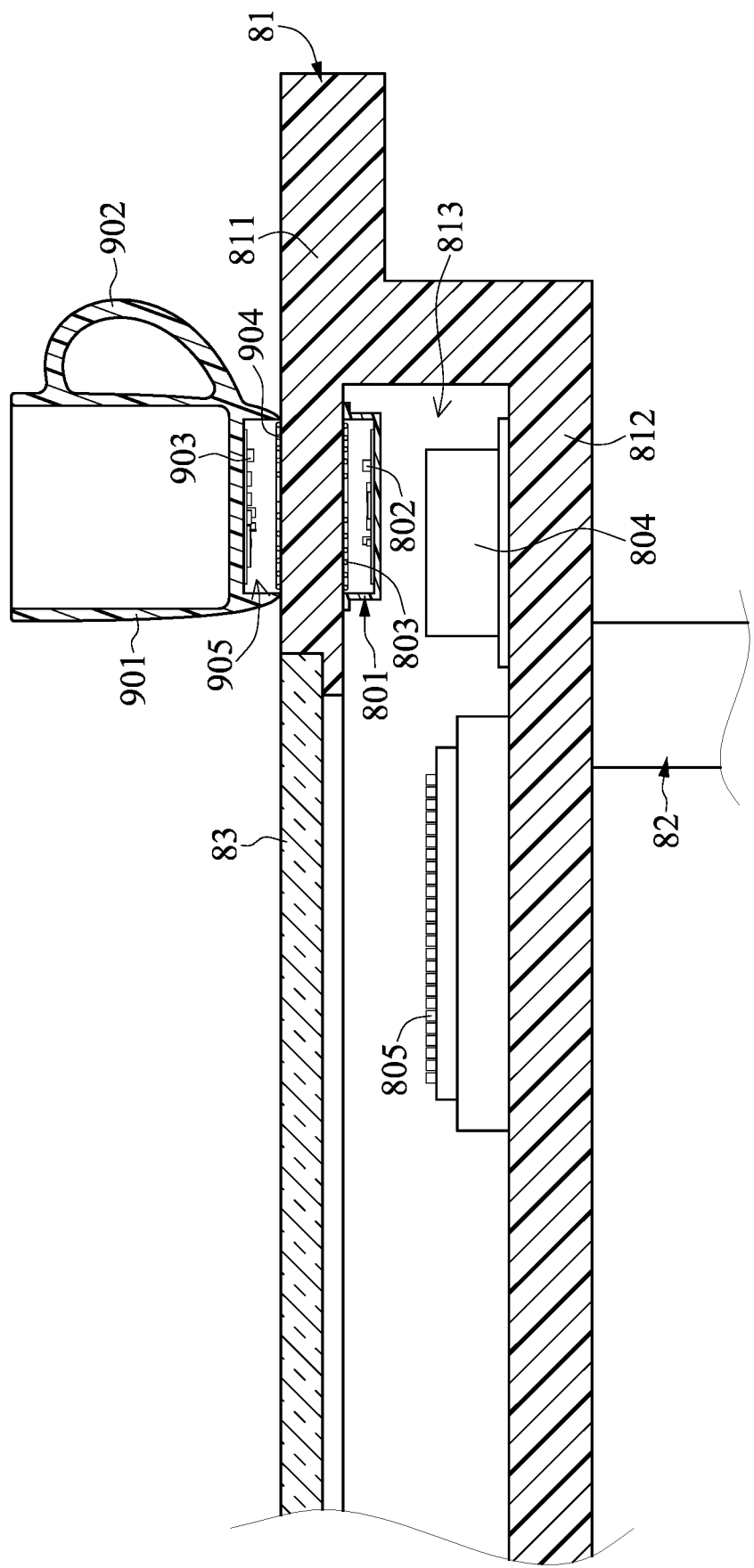
FIG. 8 is a section view taken along line VIII-VIII of FIG. 7.
Figure 9:
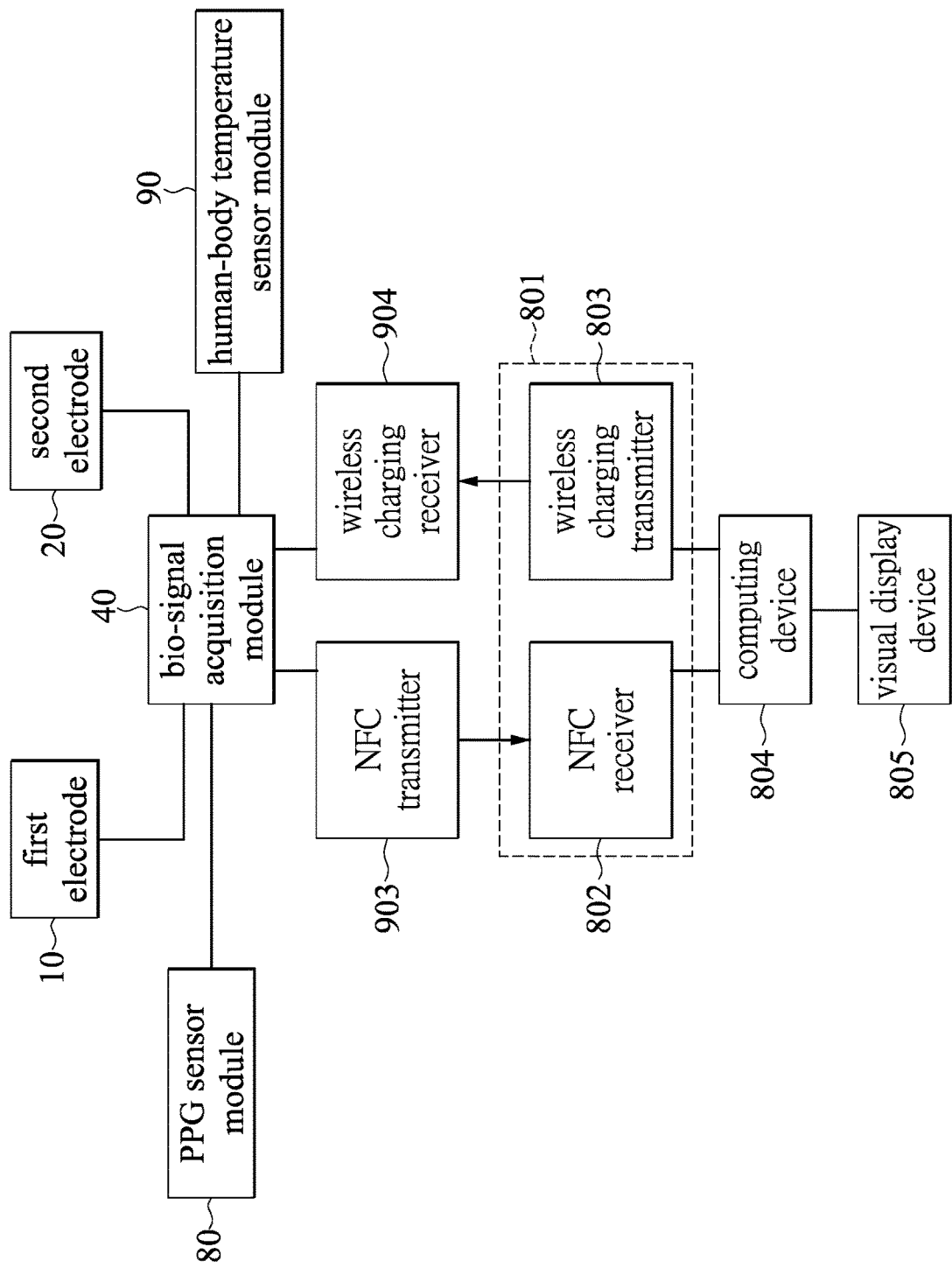
FIG. 9 is a functional block diagram of a combination table and cup of the present disclosure.

In one embodiment, as shown in FIG. 5, the bio-feedback module 50 may also be or have a quantifiable color indicator 502. The quantifiable color indicator 502 is exposed from the cup body 101 and used to provide bio-feedback according to various physiological data of the user, such as the heart rate, through the length and color changes. With the quantifiable color indicator 502, the user can more intuitively understand his/her cardiac physiological state, and it thereby provides the user with a reference index value such as the caffeine intake.

In one embodiment, the cup 100 may have an expandable PPG sensor module 80, such as a photoplethysmography (PPG) sensor. Meanwhile, the signal output by the PPG sensor module 80 is a photoplethysmography (PPG) signal.

In detail, the PPG sensor module 80 uses the optical penetration and reflection methods and the principle of the light sensing element absorbing light energy to detect changes in the amount of light absorbed and reflected by substances flowing through the blood vessels and blood when the peripheral blood vessel (such as small arteries) are pulsating. Further, since the blood flow in the blood vessels would change periodically according to heartbeat, and the PPG sensor module 80 senses the flow or concentration changes of the blood vessel tissue or blood content using the intensity of reflected light of the blood by illuminating the blood vessels under the skin with the light of different wave lengths. At the same time, the period of the PPG signal is also corresponding to the period of heartbeat. That is, the PPG signal is the electrical signal generated in response to the flow or concentration in the blood vessel tissue or blood detected by the PPG sensor module 80 using the light sensing element. This is well known to those skilled in the art and therefore will not be further described. In the present embodiment, the PPG sensor module 80 may be exposed from or built-in on the cup body 101 or the grip 102, and electrically connected to the bio-signal acquisition module 40. When the user's finger touches the PPG sensor module 80, the bio-signal acquisition module 40 can calculate physiological data of the user, such as blood oxygen saturation, as a reference for health management according to the physiological data obtained by the PPG sensor module 80. Moreover, with both the PPG signals and the ECG signals, more physiological data of the user can be estimated, such as relative blood pressure estimates.

In one embodiment, the cup 100 may have an expandable human-body temperature sensor module 90, which may be an electronic thermometer or an infrared thermometer. The human-body temperature sensor module 90 is electrically connected to the bio-signal acquisition module 40 to obtain body temperature signals when contacting the user's hands. The human-body temperature can be calculated and recorded by the bio-signal acquisition module 40 based on the electrical signal obtained by the human-body temperature sensor module 90 when the user's finger touches the human-body temperature sensor module 90.

Figure 2:
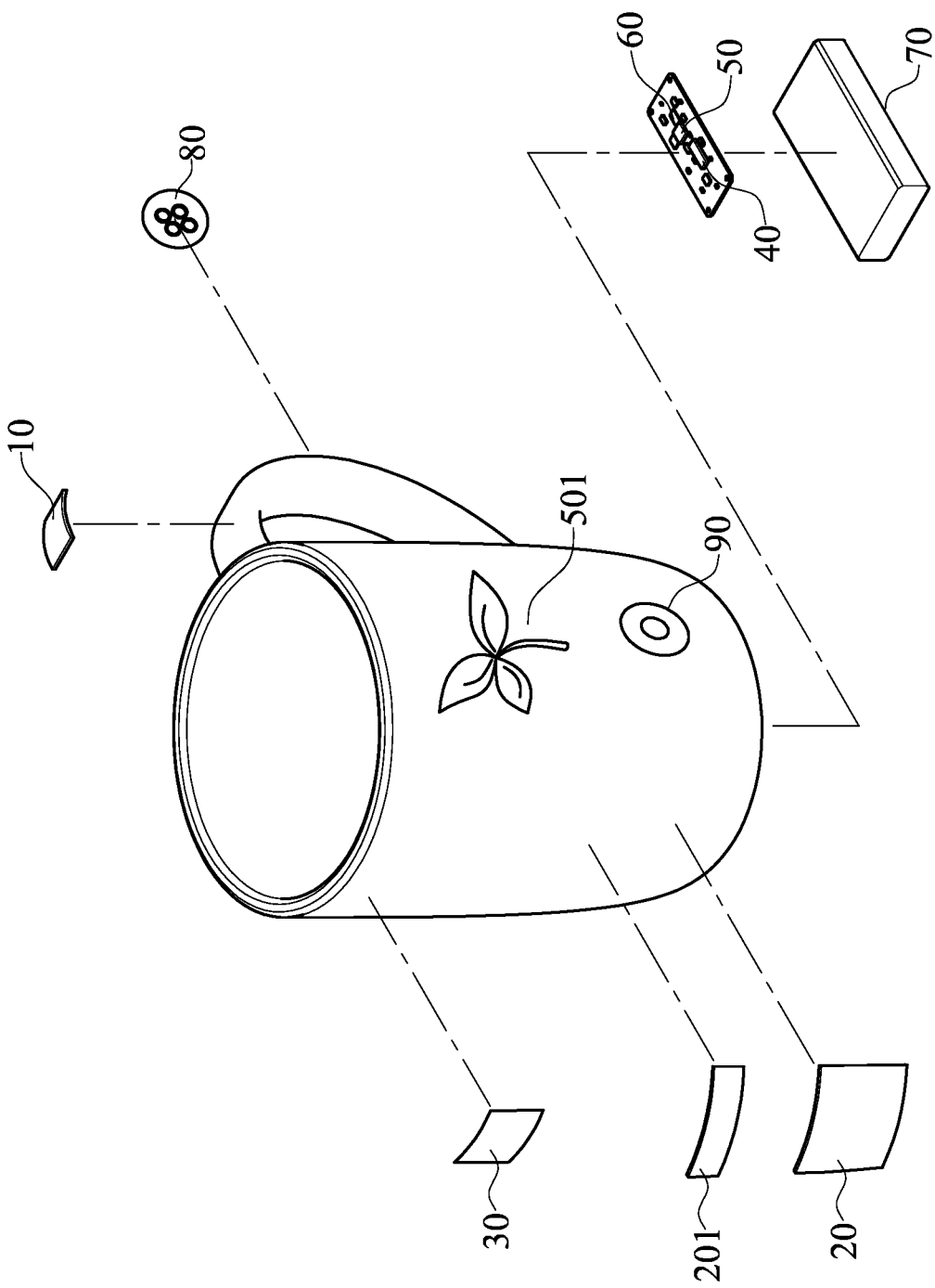
FIG. 2 is a partial exploded view of a cup of the present disclosure.
Figure 3:
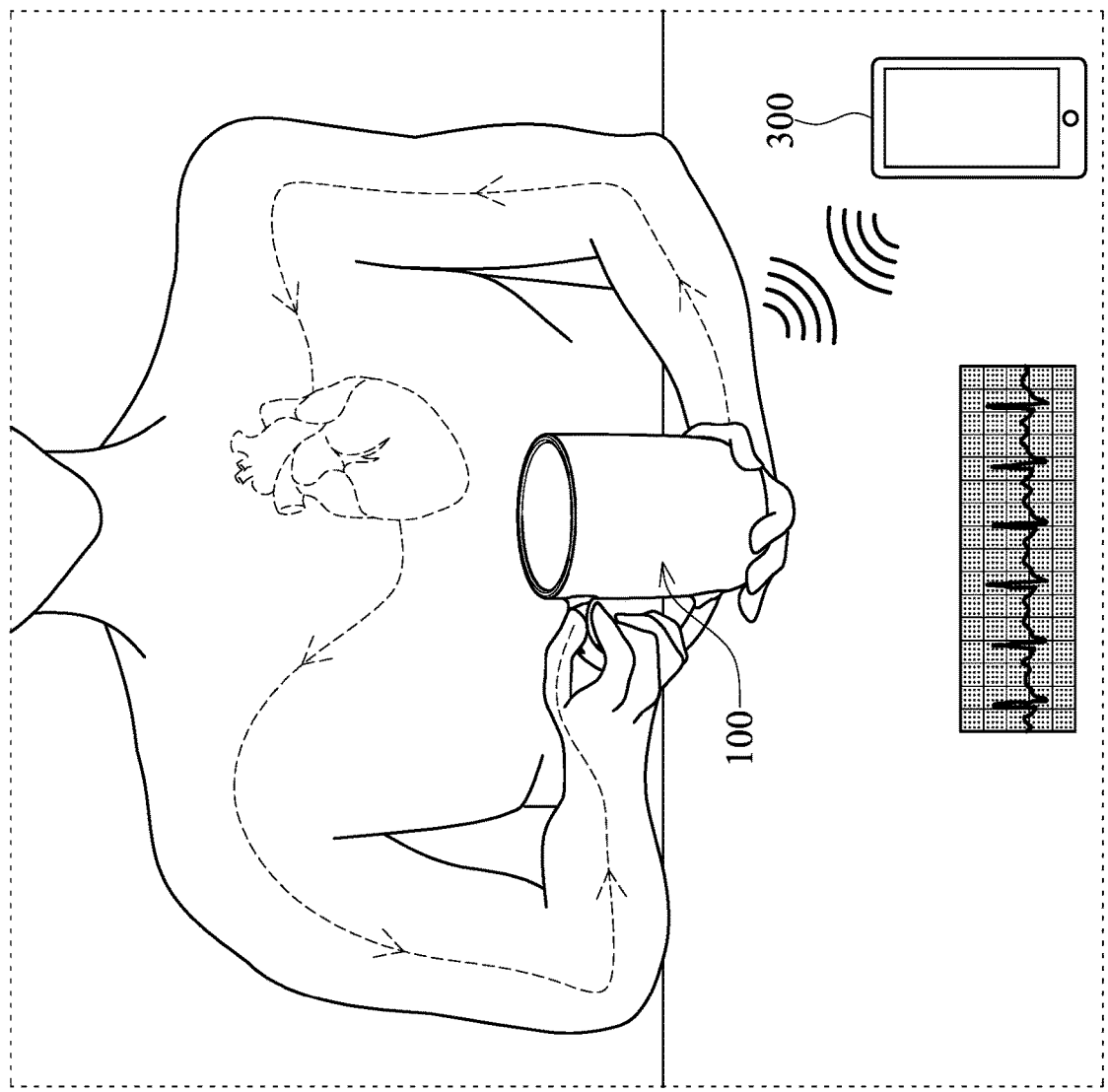
FIG. 3 is a schematic view of a cup of the present disclosure in operation.
Figure 4:
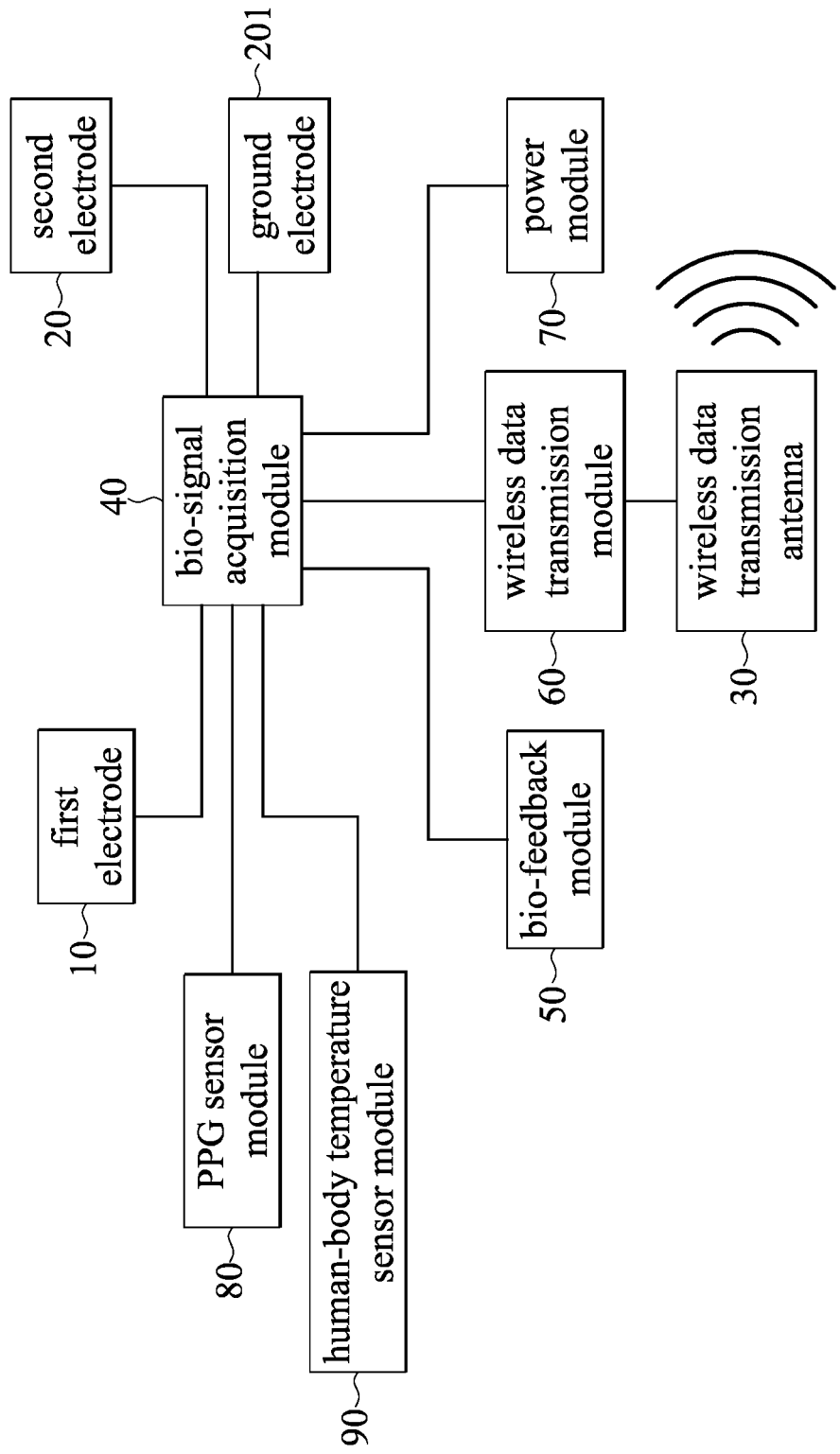
FIG. 4 is a functional block diagram of a cup of the present disclosure.

The wireless data transmission module 60 can be placed at the bottom of the cup body 101 as shown in FIG. 2 and electrically connected to the wireless data transmission antenna 30 and the bio-signal acquisition module 40. The bio-signal acquisition module 40 can send the detected raw physiological data or physiological information of the user to the bio-feedback module 50 or to the wireless data transmission module 60. The wireless data transmission module 60 sends the user's real-time physiological data through a wireless transmission manner such as Bluetooth, Wi-Fi or IR transmission technology to the electronic device 300, such as a mobile phone, a wearable device, a laptop or desktop computer, or a tablet computer, through the wireless data transmission antenna 30. After combining various algorithms on the bio-signal acquisition module 40 or the electronic device 300, various application information, such as human-body temperature, heart rate, heart rate variability, heart age, peripheral oxygen saturation, relative blood pressure, risk alert for excessive heart rate, mood index, physiological stress index, caffeine intake index, and heart risk index can be calculated.

In addition, the wireless data transmission antenna 30 may be at least one of the following: a thin metal plating layer, a thin metal coating layer, a thin metal sputter coating layer or a sheet-metal layer on the surface of the cup body 101 or the grip 102.

The power module 70 can be located at the bottom of the cup body 101 as shown in FIG. 2 and electrically connected to the bio-signal acquisition module 40 to provide the basic electric power of each module.

Referring to FIG. 6 to FIG. 9, the present disclosure further provides a combination table and cup with bio-signal acquisition and feedback capabilities (hereinafter referred to as the combination table and cup).

The combination table and cup basically includes a table 800 and a cup 900. The cup 900 may be similar to the cup 100 described previously (as shown in FIG. 1 to FIG. 5).

The cup 900 of this embodiment may include a cup body 901, a grip 902, a first electrode 10, a second electrode 20, a bio-signal acquisition module 40, a PPG sensor module 80, a human-body temperature module 90, a near field communication (NFC) transmitter 903 and a wireless charging receiver 904.

The first electrode 10, the second electrode 20, the PPG sensor module 80 and the human-body temperature module 90 can be exposed on a surface of the cup 900. The bio-signal acquisition module 40, the NFC transmitter 903 and the wireless charging receiver 904 can be concealed within an internal waterproof space 905 of the cup 900.

The bio-signal acquisition module 40 is electrically connected to the first electrode 10, the second electrode 20, the PPG sensor module 80, the human-body temperature module 90, the NFC transmitter 903 and the wireless charging receiver 904.

The bio-signal acquisition module 40 can detect the user's cardiac signal with a built-in electrocardiogram (ECG or EKG) acquisition module. The bio-signal acquisition module 40 can detect and obtain an ECG signal when the user touches the first electrode 10 and the second electrode 20 with both hands. The bio-signal acquisition module 40 can obtain a PPG signal through the PPG sensor module 80 when the user touches the PPG sensor module 80. The bio-signal acquisition module 40 can obtain a human-body temperature signal through the human-body temperature sensor module 90 when the user touches the human-body temperature sensor module 90.

The table 800 of this embodiment may include a table top 81, table legs 82, a transparent cover plate 83, one or more transceiver modules 801, a computing device 804 and a visual display device 805.

Further, the table top 81 has an upper portion 811, a lower portion 812 and an accommodation space 813 formed between the upper portion 811 and the lower portion 812. The transparent cover plate 83 is embedded in the upper portion 811. The transparent cover plate 83 is shaped in a rectangular shape corresponding to the shape of the upper portion 811, but can also be shaped in a triangle shape or various geometric shapes. The transparent cover plate 83 is made of a transparent material. The transparent material can be glass for added luxury, but can also be a high-transparency plastic material for added safety. One or more contact areas 8111 are formed on the top surface of the upper portion 811 and surround the transparent cover plate 83. Preferably, there are eight contact areas 8111 formed on the top surface of the upper portion 811 and surrounding the transparent cover plate 83. In addition, each of the contact areas can be illuminated by an illuminant, but can also be formed by a self-luminous material such as a phosphorescent material.

The transceiver modules 801 are arranged in the accommodation space 813, located at the bottom surface of the upper portion 811, and corresponding to the contact areas 8111 in position. The visual display device 805 is arranged in the accommodation space 813, located on the top surface of the lower portion 812 and underneath the transparent cover plate 83. The computing device 804 is arranged in the accommodation space 813 and located on the top surface of the lower portion 812. The computing device 804 is electrically connected to the transceiver modules 801 and the visual display device 805 for controlling them. The computing device 804 can have a built-in power module or can be electrically connected to an external power source (e.g., AC power source) to power the transceiver modules 801 and the visual display device 805. The table legs 82 are connected to the bottom surface of the lower portion 812.

Furthermore, each of the transceiver modules 801 has an NFC receiver 802 and a wireless charging transmitter 803. The wireless charging transmitter 803 can transmit electrical power through an inductive coupling to the wireless charging receiver 904 when the cup 900 is placed on the corresponding contact area 8111. The NFC receiver 802 can receive the ECG signal, the PPG signal and the human-body temperature signal transferred from the NFC transmitter 903 through a near field communication protocol when the cup 900 is placed on the corresponding contact area 8111.

The computing device 804 can provide a physiological index and an extended cardiac index of the user according to the ECG signal, the PPG signal and the human-body temperature signal, and control the visual display device 805 to display the first visual information, in the form of a light pattern or phases, corresponding to the physiological index and the extended cardiac index. Then the computing device 804 determines whether to control the visual display device 805 to display the different second visual information after comparing a value of the physiological index or the extended cardiac index with a threshold value.

Specifically, the extended cardiac index can be or include a stress index. The computing device 804 can control the visual display device 805 to display the first visual information corresponding to the value of the stress index, and compare the value with the threshold value to determine if the value exceeds the threshold value. If the value exceeds the threshold value, then the computing device 804 controls the visual display device 805 to display the second visual information, such as relaxation instructions, to instruct the user to relieve stress, so as to achieve the effect of stress relieving.

The second visual information displayed on the visual display device 805 may be more brightly-colored to attract the user's attention. The visual display device 805 may be or have an LED array display panel which can be very bright and eye-catching.

Figure 10:
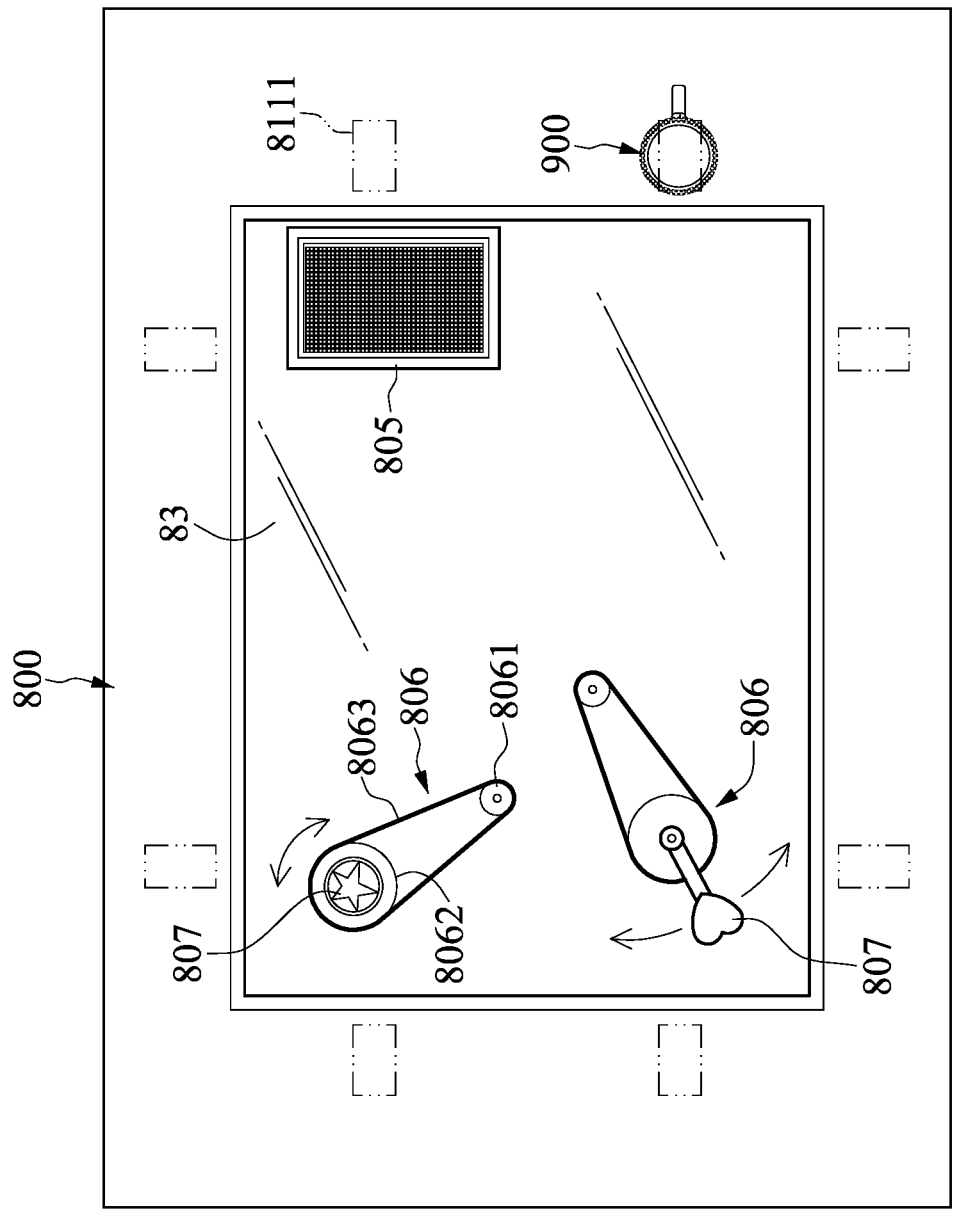
FIG. 10 is a top view of another combination table and cup of the present disclosure.
Figure 11:
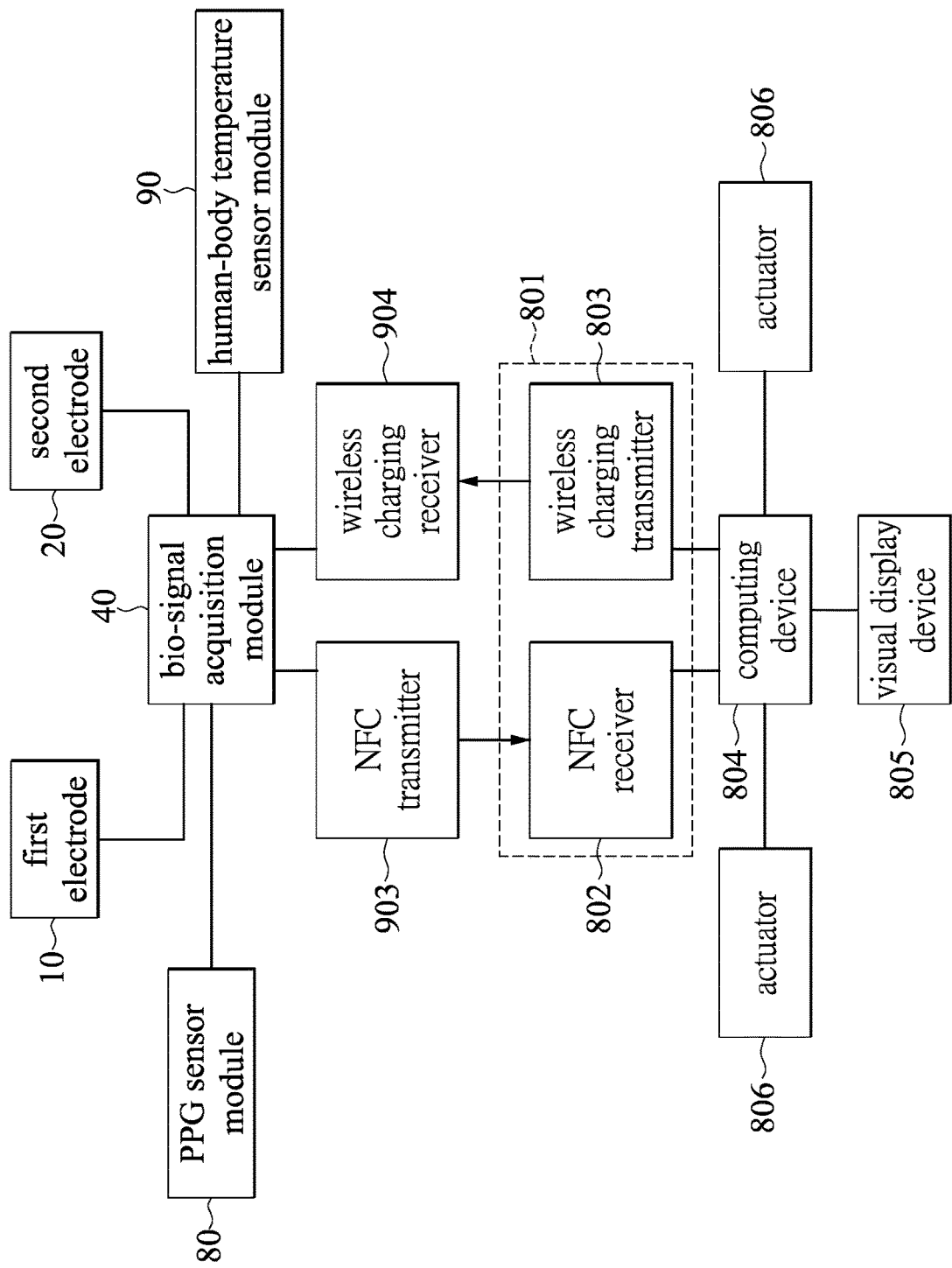
FIG. 11 is a functional block diagram of another combination table and cup of the present disclosure.

In one embodiment, as shown in FIG. 10 and FIG. 11, the table 800 can further include one or more actuators 806 and indicators 807. The actuators 806 and indicators 807 are arranged underneath the transparent cover plate 83, and the indicators 807 respectively disposed on the actuators 806 can be driven to move. Each of the indicators 807 can be provided in the form of an animal-like, humanoid, holiday figure, icon or any characters attracted, known or recognizable to children or adults. The computing device 804 is electrically connected to the actuators 806 and can control the actuators 806 to drive the indicators 807 to move in different motion trajectories. One of the motion trajectories can be used to indicate the user's stress level, and another one of the motion trajectories can be used to attract the user's attention to change the mood of the user.

The actuator 806 of this embodiment can be an electric motor-operated actuator and can include a drive pulley 8061 connected by a belt 8063 to a pulley 8062. In other embodiments, the pulleys of the actuator 806 can be replaced with a gearbox that provides a rotational output when driven by a motor.

In summary, the exemplary embodiments of the present disclosure provide a combination table and cup with bio-signal acquisition and feedback capabilities. Through the first electrode located at the cup, the second electrode located at the cup, the PPG Sensor module located at the cup, the human-body temperature sensor module located at the cup, the bio-signal acquisition module designed with ECG detecting function located inside the cup, the transparent cover plate embedded in the table top of the table, the visual display device of the table arranged underneath the transparent cover plate, the contact area formed on a top surface of the table top, the transceiver module of the table arranged corresponding to the position of the contact area and configured to transmit electrical power and receive bio-signals, and the computing device of the table configured to provide a physiological index and an extended cardiac index of the user according to the received bio-signals, the user can complete the measurement of the bio-signals while holding the cup without any additional burden on clothing coordination or being forced to change habits, and obtain the corresponding visual bio-feedback from the table when the cup is placed on the contact area of the table.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A combination table and cup with bio-signal acquisition and feedback capabilities, comprising:

a cup including a first electrode, a second electrode, a human-body temperature sensor module, a photoplethysmography (PPG) sensor module, a bio-signal acquisition module, a near field communication (NFC) transmitter and a wireless charging receiver; wherein the first electrode, the second electrode, the human-body temperature sensor module and the PPG sensor module are exposed on a surface of the cup, and the bio-signal acquisition module, the NFC transmitter and the wireless charging receiver are concealed within an internal waterproof space of the cup; wherein the bio-signal acquisition module is electrically connected to the first electrode, the second electrode, the human-body temperature sensor module, the PPG sensor module, the NFC transmitter and the wireless charging receiver; wherein the bio-signal acquisition module is configured to detect a user's cardiac signal with a built-in electrocardiogram (ECG or EKG) acquisition module; wherein the bio-signal acquisition module detects and obtains an ECG signal when the user touches the first electrode and the second electrode with both hands, wherein the bio-signal acquisition module obtains a PPG signal through the PPG sensor module when the user touches the PPG sensor module, and wherein the bio-signal acquisition module obtains a human-body temperature signal through the human-body temperature sensor module when the user touches the human-body temperature sensor module; and a table including a table top having a transparent cover plate, one or more transceiver modules each having an NFC receiver and a wireless charging transmitter, a visual display device and a computing device; wherein the table top has an upper portion, a lower portion, and an accommodation space formed between the upper portion and the lower portion; wherein the transparent cover plate is embedded in the upper portion and made of a transparent material; wherein one or more contact areas are formed on a top surface of the upper portion and surround the transparent cover plate; wherein the one or more transceiver modules are arranged in the accommodation space, located at a bottom surface of the upper portion, and corresponding to the one or more contact areas in position; wherein the visual display device is arranged in the accommodation space, located on a top surface of the lower portion and underneath the transparent cover plate; wherein the computing device is arranged in the accommodation space and located on the top surface of the lower portion; wherein the computing device is electrically connected to the one or more transceiver modules and the visual display device; wherein the wireless charging transmitter is configured to transmit electrical power through an inductive coupling to the wireless charging receiver when the cup is placed on the corresponding contact area; wherein the NFC receiver is configured to receive the ECG signal, the PPG signal and the human-body temperature signal transferred from the NFC transmitter through a near field communication protocol when the cup is placed on the corresponding contact area; wherein the computing device is configured to provide a physiological index and an extended cardiac index of the user according to the ECG signal, the PPG signal and the human-body temperature signal, and control the visual display device to display a first visual information corresponding to the physiological index and the extended cardiac index, and then determine whether to control the visual display device to display a different second visual information after comparing a value of the physiological index or the extended cardiac index with a threshold value.

2. The combination table and cup according to claim 1, wherein the table further includes a plurality of actuators and a plurality of indicators, the actuators and the indicators are arranged in the accommodation space and underneath the transparent cover plate, the indicators are respectively disposed on the actuators, and the computing device is electrically connected to the actuators and configured to control the actuators to drive the indicators to move in different motion trajectories.

3. The combination table and cup according to claim 2, wherein each of the actuators is an electric motor-operated actuator.

4. The combination table and cup according to claim 1, wherein the transparent material is glass.

5. The combination table and cup according to claim 1, wherein the transparent material is a high-transparency plastic material.

6. The combination table and cup according to claim 1, wherein the contact area is formed by a self-luminous material.

7. The combination table and cup according to claim 1, wherein the physiological index that can be used as instant feedback to the user and can be recorded, includes any one or more of human-body temperature, heart rate (beats per minute, BPM), heart rate variability (HRV), peripheral oxygen saturation (SpO2), heart age, blood pressure estimates and risk alert for excessive heart rate.

8. The combination table and cup according to claim 7, wherein the extended cardiac index that can be determined by a preset algorithm according to physiological data, ECG data and PPG data of the user, is a mood index, a stress index, a caffeine intake index or a heart risk index.

9. The combination table and cup according to claim 1, wherein the computing device of the table is provided with a built-in power module and the power module is a replaceable battery module or a rechargeable battery module.

10. The combination table and cup according to claim 1, wherein the computing device of the table is electrically connected to an external power source.

\* \* \* \* \*